United States Patent
Liu et al.

(10) Patent No.: US 11,946,088 B2
(45) Date of Patent: Apr. 2, 2024

(54) METHOD FOR PROCESSING OIL CROPS WITH RHODOTORULA

(71) Applicant: Jiangnan University, Wuxi (CN)

(72) Inventors: Yuanfa Liu, Wuxi (CN); Zhongyang Ding, Wuxi (CN); Yunzhi Jiang, Wuxi (CN); Liting Zhao, Wuxi (CN); Mengmeng Xu, Wuxi (CN); Qi Zhang, Wuxi (CN); Zhenghua Gu, Wuxi (CN); Guiyang Shi, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 281 days.

(21) Appl. No.: 17/351,322

(22) Filed: Jun. 18, 2021

(65) Prior Publication Data

US 2021/0310035 A1 Oct. 7, 2021

Related U.S. Application Data

(63) Continuation of application No. PCT/CN2018/123816, filed on Dec. 26, 2018.

(30) Foreign Application Priority Data

Dec. 19, 2018 (CN) .......................... 201811553634.4

(51) Int. Cl.
*C12P 23/00* (2006.01)
*C12N 1/16* (2006.01)
*C12P 7/6436* (2022.01)

(52) U.S. Cl.
CPC ................ *C12P 23/00* (2013.01); *C12N 1/16* (2013.01); *C12P 7/6436* (2013.01)

(58) Field of Classification Search
None
See application file for complete search history.

(56) References Cited

U.S. PATENT DOCUMENTS

2016/0265009 A1 9/2016 Slininger et al.

FOREIGN PATENT DOCUMENTS

| CN | 101006182 A | 7/2007 | |
|---|---|---|---|
| CN | 104130952 A | 11/2014 | |
| CN | 109536268 A | 3/2019 | |
| WO | WO-2010120939 A2 * | 10/2010 | ............. A23K 10/37 |

OTHER PUBLICATIONS

Roadjanakamolson, M., and Worapot Suntornsuk. "Production of β-carotene-enriched rice bran using solid-state fermentation of Rhodotorula glutinis." Journal of microbiology and biotechnology 20.3 (2010): 525-531. (Year: 2010).*
Sun, JiaJing, et al. "The solid-state fermentation process of Rhodotorula mucilaginosa for producing carotenoids." Scientia Agricultura Sinica 51.10 (2018): 1982-1994. (Year: 2018).*
Yu, Dianyu, et al. "Optimal extrusion pretreatment process improving quality of soybean protein powder." Transactions of the Chinese Society of Agricultural Engineering 34.4 (2018): 285-292. (Year: 2018).*
Mukherjee, Runni, Runu Chakraborty, and Abhishek Dutta. "Role of fermentation in improving nutritional quality of soybean meal—a review." Asian-Australasian journal of animal sciences 29.11 (2016): 1523. (Year: 2016).*

* cited by examiner

*Primary Examiner* — Robert J Yamasaki
(74) *Attorney, Agent, or Firm* — IPRO, PLLC; Na Xu

(57) ABSTRACT

The disclosure discloses a method for processing oil crops with *rhodotorula*, and belongs to the technical field of fermentation. The method includes the step of inoculating the *rhodotorula* (such as *Rhodotorula mucilaginosa*, *Sporidiobolus salmonicolor* and *Rhodotorula glutinis*) that can produce carotenoid into a fermentation medium that contains oil-rich oil crops for solid state fermentation to obtain oil and oil crop meal rich in carotenoid. The carotenoid as a fermentative metabolite of the *rhodotorula* has bioactivities of resisting oxidation, preventing vascular sclerosis, enhancing immunity and preventing cancers. Contents of carotenoid in the oil and oil crop meal acquired by the method can be up to 9.071 μg/g and 8.062 μg/g correspondingly. By the method, the oil and oil crop meal rich in carotenoid can be acquired at the same time by just once fermentation and once oil pressing without additional functional substances, and thus the production cost of the functional oil and the fermentation oil crop meal is greatly reduced.

8 Claims, 1 Drawing Sheet

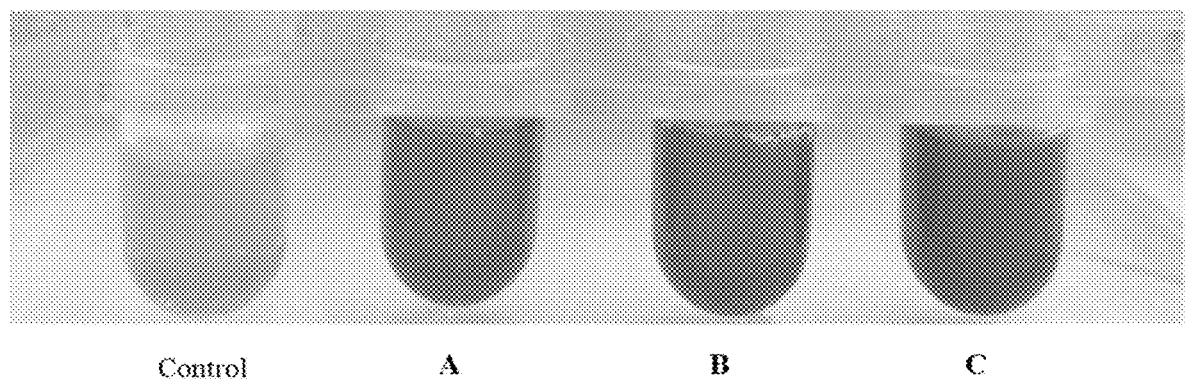
Control    A    B    C

METHOD FOR PROCESSING OIL CROPS WITH RHODOTORULA

TECHNICAL FIELD

The disclosure relates to a method for processing oil crops with *rhodotorula*, and belongs to the technical field of fermentation.

BACKGROUND

Soybean is an important crop for grain and oil in the world and about 85% of global soybean yield is used for oil pressing, so it is the main global source of vegetable oil and protein feed. Existing soybean processing technologies for preparing soybean oil and soybean meal mainly extruding soybeans first, pressing oil from the extruded soybeans to obtain the soybean oil, and then drying residues to obtain the soybean meal. The soybean oil pressed from soybeans is an excellent edible oil which has a quite high nutritional value, and it is one of the most common edible oils in daily life of people; and the soybean meal, as a byproduct, that is acquired after pressing oil from the soybeans is huge in yield and is an excellent plant protein source for a culture feed due to its protein content up to 45% or more and reasonable amino acid composition.

In terms of soybean oil, at present, with the continuous improvement of the quality of life, consumers have higher and higher requirements on the quality of edible oils. In order to gain the favor of consumers, researchers and manufacturers of edible oils have been trying to add natural functional substances (such as carotenoid, squalene and flavone) into soybean oil to endow the soybean oil with certain bioactivities, so that obtained products, functional oils, not only have higher market competitiveness, but also have an improved additional value. However, those natural functional substances require a process of production, extraction and preparation; thus, such oil products have a defect of long technological process in production or natural functional substance products need to be purchased for addition at a high cost.

In terms of soybean meal, researchers and manufacturers of feed often carry out microbial fermentation of bean meal to further improve the quality of the bean meal. However, the fermented bean meal needs a plurality of links of water adding and material mixing, raw material sterilizing, inoculating and fermenting and drying; thus, although the quality of the bean meal is improved, the production cost is greatly increased, which is an important problem to be solved for a feed and culture industry that needs to strictly control cost.

SUMMARY

In order to solve the aforementioned problems, the disclosure provides a method for fermentation processing of soybean extruded powder or other oil crop powder with *rhodotorula*. The method includes the step of inoculating the *rhodotorula* (such as *Rhodotorula mucilaginosa*, *Sporidiobolus salmonicolor* and *Rhodotorula glutinis*) that can produce carotenoid into a fermentation medium that contains oil-rich oil crops (such as extruded soybeans, peanuts and rapeseeds) for solid state fermentation to obtain oil and oil crop meal rich in carotenoid. The carotenoid as a fermentative metabolite of the *rhodotorula* has bioactivities of resisting oxidation, preventing vascular sclerosis, enhancing immunity and preventing cancers. Contents of carotenoid in the oil and oil crop meal acquired by the method can be up to 9.071 µg/g and 8.062 µg/g correspondingly. By the method, the oil and oil crop meal rich in carotenoid can be acquired at the same time by just once fermentation and once oil pressing without the need of additional functional substances, and thus the production cost of the functional oil and the fermentation oil crop meal is greatly reduced.

Technical Scheme of the Disclosure is as Follows

The disclosure provides a method for processing oil crops with *rhodotorula*, which includes the steps of inoculating *rhodotorula* that may produce carotenoid into a fermentation medium that contains oil crop powder and water for solid state fermentation to obtain a solid state fermented product; and pressing oil from the fermented product to obtain oil and oil crop meal.

The oil crop powder includes one or more of soybean extruded powder, soybean powder, peanut powder, rapeseed powder, castor powder and sesame powder.

In one embodiment of the disclosure, the fermentation medium includes, by mass, the oil crop powder, 35-45% of a total mass of the fermentation medium and the water, 55-65% of the total mass of the fermentation medium.

In one embodiment of the disclosure, the fermentation medium includes the oil crop powder 40% of the total mass of the fermentation medium and the water, 60% of the total mass of the fermentation medium.

In one embodiment of the disclosure, conditions for the solid state fermentation include a temperature of 25-30° C. and a time of 3-6 d.

In one embodiment of the disclosure, conditions for the solid state fermentation include a temperature of 30° C. and a time of 4 d.

In one embodiment of the disclosure, inoculating the *rhodotorula* into the fermentation medium for solid state fermentation is inoculating a bacteria solution of *rhodotorula* into the fermentation medium with for solid state fermentation; and an inoculum size of the bacteria solution of *rhodotorula* in the fermentation medium is that a volume of the inoculated bacteria solution of *rhodotorula* is 10-15% of a mass of the oil crop powder, and a cell concentration of the inoculated bacteria solution of *rhodotorula* is $1 \times 10^8$-$1 \times 10^{10}$ CFU/mL. 10-15% refers to that each 100 g of the oil crop powder is inoculated with 10-15 mL of the bacteria solution of *rhodotorula*.

In one embodiment of the disclosure, the *rhodotorula* includes one or more of *Rhodotorula mucilaginosa*, *Sporidiobolus salmonicolor* and *Rhodotorula glutinis*.

In one embodiment of the disclosure, the *rhodotorula* is *Rhodotorula glutinis*.

In one embodiment of the disclosure, the fermentation medium includes the soybean extruded powder and the water.

The disclosure further provides oil and bean meal or other oil crop meal prepared by the method above.

The disclosure further provides a product that contains the oil and/or oil meal above or other oil crop meal.

In one embodiment of the disclosure, the product is a feed, a food, a drug or a healthcare product.

Beneficial Effects (1) The oil prepared by the method has rich carotenoid with its content up to 9.071 µg/g, so it has functions of resisting oxidation, delaying ageing, enhancing immunity and preventing cancers and also has great application prospects in the fields of food, drugs and healthcare products.

(2) Existing functional oil is acquired by preparing and extracting nutrients and mixing the oil with various nutrients that have a regulation effect on human health, so it has the defects of complicated process and high cost. In the disclosure, functional oil rich in carotenoid is acquired by directly inoculating the *rhodotorula* that can produce bioactive components into the fermentation medium formed by mixing the oil-rich oil crop (such as extruded soybeans, peanuts and rapeseeds) powder and water for solid state fermentation, which is simple in operation and low in cost.

(3) Oil crop meal such as bean meal, peanut meal and rapeseed meal prepared by the method of the disclosure also has rich carotenoid with its content up to 8.062 μg/g, so it has certain functions of resisting oxidation, delaying ageing, enhancing immunity and preventing cancers and has great application prospects in preparation of high quality feed.

(4) Existing manufactures of feed often sterilize oil crops subjected to oil pressing and ferment the sterilized oil crops and various kinds of bacteria to obtain a fermented bean meal feed, as a result, sterilizing, fermenting and other additional processes are added to processing of the feed, which greatly increases the cost of the feed. In the disclosure, the oil crop meal is acquired by directly inoculating the *rhodotorula* that can produce bioactive components into the fermentation medium formed by mixing oil-rich oil crop (such as extruded soybeans, peanuts and rapeseeds) powder and water for solid state fermentation, and pressing oil, and it has already achieved original purposes and significance of fermentation of the oil crop meal, and the operation steps are reduced at the same time, greatly reducing the cost of feed.

(5) Manufacturers of feed usually add a large quantity of antibiotics to feed to reduce the survival rate of bred animals, and undoubtedly, a lot of antibiotics will be left in bodies of the bred animals, resulting in potential hazards to health food sanitation and safety. In the disclosure, the oil crop meal with rich carotenoid and functions of resisting oxidation, delaying ageing, enhancing immunity and preventing cancers is acquired by directly inoculating the *rhodotorula* that can produce bioactive components into the fermentation medium formed by mixing oil-rich oil crop (such as extruded soybeans, peanuts and rapeseeds) powder and water for solid state fermentation, and it has great potential to completely or partly replace antibiotics in feed to realize an effect of improving the survival rate of the bred animals.

BRIEF DESCRIPTION OF FIGURES

FIG. 1 shows functional oil acquired by extraction after solid state fermentation of extruded soybeans with different kinds of *rhodotorula*.

DETAILED DESCRIPTION

The disclosure is further described in conjunction with Examples as follows.

*Rhodotorula mucilaginosa*, *Sporidiobolus salmonicolor* and *Rhodotorula glutinis* involved in following Examples are all purchased from the China General Microbiological Culture Collection Center and have serial numbers: CGMCC No. 2.5511, CGMCC No. 2.4290 and CGMCC No. 2.5570 correspondingly; and soybean extruded powder involved in following Examples comes from Shandong Bohai Oil Industry Co., Ltd., and peanut powder and rapeseed powder are both purchased from farmer's markets in Wuxi (*Rhodotorula mucilaginosa* CGMCC No. 2.5511, *Sporidiobolus salmonicolor* CGMCC No. 2.4290 and *Rhodotorula glutinis* CGMCC No. 2.5570 can all be purchased and do not need deposit for patent procedure).

A Medium Involved in Following Examples is as Follows

A YPD seed medium (m/v): peptone 2%, yeast 1% and glucose 2%.

Detection Methods Involved in Following Examples are as Follows

Analysis of Functional Oil and Oil Crop Meal:
1. Extraction

A solid state fermented product is dried at 50° C. until a water content reaches 5-10%; the dried fermented product and n-hexane are mixed at a mass ratio of 1:30, soaked and stirred for 24 h; suction filtration is performed and a filtrate is taken; and the filtrate is rotary evaporated at 50° C. by a rotary evaporator to obtain the functional oil and oil crop meal.

2. Measurement of Type and Content of Fatty Acid in Functional Oil 50 mg of the acquired functional oil is taken and added to 2 mL of a 0.5 mol/L NaOH—$CH_3OH$ solution; the mixture is saponified in a water bath for 30 min at 65° C., cooled to room temperature, and 2 mL of a 14% $BF_3$—$CH_3OH$ solution is added; the mixture is saponified in a water bath for 30 min at 65° C., cooled to room temperature, and 5 mL of n-hexane is added to oscillate for 3-4 min to extract fatty acid methyl ester; a little of anhydrous $Na_2SO_4$ is added for dewatering treatment; centrifuging is performed for 5 min at 10,000 r/min; an upper layer organic phase is taken to pass through a 0.22 μm organic film for use; a 0.2 mg/mL nonadecanoic acid methylester solution (with n-hexane as a solvent) is added to a solution subjected to methyl esterification and film passing at a volume ratio of 1:1 to serve as an internal standard; and the content of the fatty acid in the extract is measured by a GC-MS.

3. Extraction and Content Measurement of Carotenoid in Functional Oil (1) 0.5 g of functional oil is accurately weighed and added into a 10 mL brown glass volumetric flask, reaches a constant volume with dichloromethane and is shaken up, and its OD value is measured at a light absorption wavelength of 450 nm and is substituted into a standard curve to calculate the content of the carotenoid.

(2) the standard curve of the content of the carotenoid is formulated: a 0.2 mg/mL β-carotene standard solution is prepared, 0, 0.1, 0.2, 0.4, 0.8, 1.6, 3.2 and 6.4 mL of β-carotene standard solutions are sucked correspondingly to reach a constant volume 10 mL with dichloromethane, their OD values are measured at a light absorption wavelength of 450 nm, and a standard product curve is drawn.

4. Extraction and Content Measurement of Carotenoid in Oil Crop Meal 500 mg of oil crop meal is accurately weighed and put into a brown flask, 5 mL of acetone is added for ultrasonic treatment for 2 h, and the flask is taken out and shaken up every 20 min; the solution is centrifuged for 10 min at 10,000 rpm after ultrasonic treatment, and a supernate is taken; and the content of the carotenoid in the oil crop meal is measured by the measurement method for the content of the carotenoid in the functional oil.

Detection Method of Cell Concentration:

1 mL of a seed solution of *rhodotorula* is taken to a cuvette, $OD_{600}$ is measured, then the seed solution is diluted with normal saline, the number of cells of the *rhodotorula* is counted by a 25×16 blood counting chamber, and the cell concentration is calculated.

The cell number in each mL=(cell number counted by blood counting chamber/80)×400×10000×dilution ratio.

Example 1: Using Soybean Extruded Powder as Raw Material

Specific steps are as follows:
(1) a strain of *rhodotorula* preserved at 4° C. is inoculated into a YPD seed medium (sterilized for 20 min at 115° C.) for culturing for 2 d at 30° C. and a rotating speed of 200 r·min$^{-1}$ to obtain activated fluid.
(2) 80 mL of the YPD seed medium is taken and put into a 250 mL conical flask (sterilized for 20 min at 115° C.) and 200 μL of the activated fluid obtained in step (1) is inoculated into the YPD seed medium for culturing for 2 d at a temperature of 30° C. and a rotating speed of 200 r·min$^{-1}$ to obtain a seed solution, where a cell concentration in the seed solution is about 9×10$^9$ CFU/mL at the moment.
(3) 300 g of a fermentation medium is taken and put into a 2500 mL conical flask (sterilized for 30 min at 121° C.), and the seed solution is inoculated into the fermentation medium in accordance with fermentation parameters in Table 1 for solid state fermentation to obtain a fermented product.

Oil extraction is performed on the obtained fermented product by the analysis method of the functional oil and oil crop meal to obtain the functional oil and fermented bean meal; and the obtained functional oil and fermented bean meal are analyzed by the analysis method of the functional oil and oil crop meal, and analysis results are shown in Tables 2-4. The blank group is original soybean extruded powder without microbial fermentation.

The functional oil obtained by the original soybean extruded powder, group A, group B and group C is shown in FIG. 1, and the functional oil extracted from original extruded soybeans is golden yellow, the functional oil obtained by group A is light orange, the functional oil obtained by group B has a darker color than group A and is reddish orange, and the functional oil obtained by group C has the darkest color and is almost red.

TABLE 1

Fermentation parameters

| Group | Strain | Inoculum Size | Fermentation Medium | conditions |
|---|---|---|---|---|
| Group A | Group A1 *Rhodotorula mucilaginosa* | 12 mL | Soybean extruded powder 120 g, water 180 g | 30° C., 4 d |
| | Group A2 *Rhodotorula mucilaginosa* | 21 mL | Soybean extruded powder 140 g, water 160 g | 25° C., 4 d |
| | Group A3 *Rhodotorula mucilaginosa* | 13 mL | Soybean extruded powder 110 g, water 190 g | 28° C., 6 d |

TABLE 1-continued

Fermentation parameters

| Group | Strain | Inoculum Size | Fermentation Medium | conditions |
|---|---|---|---|---|
| Group B | Group B1 *Sporidiobolus salmonicolor* | 18 mL | Soybean extruded powder 120 g, water 180 g | 30° C., 4 d |
| | Group B2 *Sporidiobolus salmonicolor* | 18 mL | Soybean extruded powder 140 g, water 160 g | 25° C., 4 d |
| | Group B3 *Sporidiobolus salmonicolor* | 16.5 mL | Soybean extruded powder 110 g, water 190 g | 28° C., 6 d |
| Group C | Group C1 *Rhodotorula glutinis* | 18 mL | Soybean extruded powder 120 g, water 180 g | 30° C., 4 d |
| | Group C2 *Rhodotorula glutinis* | 14 mL | Soybean extruded powder 140 g, water 160 g | 25° C., 4 d |
| | Group C3 *Rhodotorula glutinis* | 14 mL | Soybean extruded powder 110 g, water 190 g | 28° C., 6 d |

TABLE 2

Content of carotenoid in functional oil and fermented bean meal

| Group | | Carotenoid Oil (μg/g functional oil) | Bean meal (μg/g fermented bean meal) |
|---|---|---|---|
| Blank Group | | 7.286 | 0.623 |
| Group A | Group A1 | 7.513 | 8.062 |
| | Group A2 | 7.652 | 7.975 |
| | Group A3 | 7.751 | 8.059 |
| Group B | Group B1 | 8.462 | 2.161 |
| | Group B2 | 8.367 | 2.059 |
| | Group B3 | 8.453 | 2.112 |
| Group C | Group C1 | 9.071 | 7.627 |
| | Group C2 | 8.976 | 7.484 |
| | Group C3 | 9.031 | 7.575 |

TABLE 3

Type and content of fatty acid in functional oil (mg/g functional oil)

| | Blank Group | Group A | | |
|---|---|---|---|---|
| | | Group A1 | Group A2 | Group A3 |
| C14:0 | 0.305 | 0.268 | 0.254 | 0.276 |
| C16:0 | 46.976 | 44.832 | 45.667 | 48.492 |
| C16:1 | 0.406 | 0.387 | 0.362 | 0.435 |
| C18:0 | 16.803 | 16.122 | 16.101 | 16.556 |
| C18:1 | 108.598 | 108.652 | 107.576 | 109.112 |
| C18:2 | 223.761 | 223.592 | 221.347 | 225.379 |
| C18:3 | 25.015 | 24.394 | 23.560 | 23.673 |
| C20:0 | 1.515 | 1.400 | 1.297 | 1.378 |
| C20:1 | 1.0521 | 1.018 | 0.984 | 1.027 |
| C22:0 | 1.713 | 1.604 | 1.542 | 1.669 |
| SFA/UFA | 0.186 | 0.179 | 0.183 | 0.190 |

TABLE 4

Type and content of fatty acid in functional oil (mg/g functional oil)

| | Group B | | | Group C | | |
|---|---|---|---|---|---|---|
| | Group B1 | Group B2 | Group B3 | Group C1 | Group C2 | Group C3 |
| C14:0 | 0.361 | 0.314 | 0.372 | 0.333 | 0.320 | 0.354 |
| C16:0 | 54.176 | 52.880 | 56.076 | 45.284 | 44.187 | 46.583 |
| C16:1 | 0.589 | 0.525 | 0.587 | 0.541 | 0.512 | 0.564 |
| C18:0 | 19.640 | 18.352 | 19.896 | 16.494 | 16.087 | 16.809 |
| C18:1 | 124.662 | 121.672 | 126.176 | 119.285 | 118.817 | 121.304 |

TABLE 4-continued

Type and content of fatty acid in functional oil
(mg/g functional oil)

| | Group B | | | Group C | | |
|---|---|---|---|---|---|---|
| | Group B1 | Group B2 | Group B3 | Group C1 | Group C2 | Group C3 |
| C18:2 | 253.395 | 250.768 | 254.098 | 236.165 | 234.734 | 236.189 |
| C18:3 | 28.553 | 26.125 | 29.174 | 25.428 | 24.126 | 25.765 |
| C20:0 | 1.748 | 1.720 | 1.759 | 1.457 | 1.217 | 1.468 |
| C20:1 | 1.207 | 1.163 | 1.213 | 1.113 | 1.089 | 1.119 |
| C22:0 | 2.019 | 1.986 | 1.987 | 1.729 | 1.703 | 1.790 |
| SFA/UFA | 0.191 | 0.188 | 0.195 | 0.171 | 0.167 | 0.174 |

Note:
SFA refers to saturated fatty acid; MUFA refers to monounsaturated fatty acid; PUFA refers to polyunsaturated fatty acid; and UFA refers to unsaturated fatty acid.

It can be known from Table 2 that the functional ingredient carotenoid is added to both the functional oil and bean meal obtained by fermenting the extruded soybeans with the *rhodotorula* and further processing, and the oil is endowed by the carotenoid with physiological functions of increasing immunity of a host, preventing vascular sclerosis, restraining tumors, resisting oxidation and retraining free radicals. It can be known from Tables 3-4 that the contents of different fatty acids in the functional oil do not obviously change, but there is rich unsaturated fatty acid; thus, the functional oil prepared in the disclosure has a better healthcare function.

Example 2: Using Peanut Powder as Raw Material

Specific Steps are as Follows:
(1) The same as Example 1.
(2) The same as Example 1.
(3) Peanuts are put into a hot air circulating oven and dried at 50° C. until a water content reaches 5-10%, then the peanuts are husked, and the husked peanuts are ground into fine peanut powder.
(4) The peanut powder replaces soybean extruded powder, and 300 g of a fermentation medium is taken and put into a 2500 mL conical flask (sterilized for 30 min at 121° C.) and a seed solution is inoculated into the fermentation medium in accordance with the fermentation parameters in Table 1 for solid state fermentation to obtain a fermented product.

Oil extraction is performed on the obtained fermented product by the analysis method of the functional oil and oil crop meal to obtain the functional oil and fermented bean meal; after the obtained functional oil and fermented bean meal are analyzed by the analysis method of the functional oil and oil crop meal, it is found that the peanut oil and peanut meal both have rich carotenoid; and the presence of the carotenoid endow the oil certain physiological functions, improves the quality of the peanut meal, and comprehensively improves the nutritional values of the oil and peanut meal.

Example 3: Using Rapeseed Powder as Raw Material

Specific Steps are as Follows:
(1) The same as Example 1.
(2) The same as Example 1.
(3) Rapeseeds are put into a hot air circulating oven and dried at 50° C. until a water content reaches 5-10%, then the rapeseeds are husked, and the husked rapeseeds are ground into fine rapeseed powder.
(4) The rapeseed powder replaces soybean extruded powder, and 300 g of a fermentation medium is taken and put into a 2500 mL conical flask (sterilized for 30 min at 121° C.) and a seed solution is inoculated into the fermentation medium in accordance with the fermentation parameters in Table 1 for solid state fermentation to obtain a fermented product.

Oil extraction is performed on the obtained fermented product by the analysis method of the functional oil and oil crop meal to obtain the functional oil and fermented bean meal; after the obtained functional oil and fermented bean meal are analyzed by the analysis method of the functional oil and oil crop meal, it is found that the rapeseed oil and rapeseed meal both have rich carotenoid; and the presence of the carotenoid endows the oil certain physiological functions, improves the quality of the rapeseed meal, and comprehensively improves the nutritional values of the oil and rapeseed meal.

What is claimed is:

1. A method for producing soybean oil and oil crop meal rich in carotenoid, which comprises:
   inoculating *rhodotorula* that produces carotenoid into a fermentation medium comprising oil crop powder;
   incubating the fermentation medium with *rhodotorula* for 4 to 6 days under conditions that cause fermentation, thereby obtaining a fermented product; and
   pressing oil from the fermented product to obtain oil and oil crop meal;
   wherein the fermentation is a solid state fermentation;
   wherein the oil crop powder consists of soybean powder, and
   wherein the oil and/or the oil crop meal comprise carotenoid at a concentration of up to 9.071 μg/g of the oil and a concentration of up to 7.627 μg/g of the oil crop meal.

2. The method of claim 1, wherein the fermentation medium is a mixture of oil crop powder and water.

3. The method of claim 2, wherein the fermentation medium comprises, by mass, the oil crop powder which is 35% to 45% of a total mass of the fermentation medium and the water which is 55% to 65% of the total mass of the fermentation medium.

4. The method of claim 3, wherein the fermentation medium consists of the oil crop powder which is 40% the total mass of the fermentation medium and the water which is 60% the total mass of the fermentation medium.

5. The method of claim 1, wherein a volume of inoculated bacteria solution of *rhodotorula* is 10% to 15% of a mass of the oil crop powder; and a cell concentration of the inoculated bacteria solution of *rhodotorula* is $1\times10^8$ CFU/mL to $1\times10^{10}$ CFU/mL.

6. The method of claim 5, wherein the *rhodotorula* comprises one or more of *Rhodotorula mucilaginosa, Sporidiobolus salmonicolor* and *Rhodotorula glutinis*.

7. The method of claim 6, wherein the *rhodotorula* is *Rhodotorula glutinis*.

8. The method of claim 7, wherein the fermentation medium comprises the soybean extruded powder and water.

* * * * *